United States Patent [19]

Maehara et al.

[11] Patent Number: 4,533,082
[45] Date of Patent: Aug. 6, 1985

[54] PIEZOELECTRIC OSCILLATED NOZZLE

[75] Inventors: Naoyoshi Maehara, Nara; Kenkichi Hashido, Yamatokoriyama; Hiroshi Hirata, Nara, all of Japan

[73] Assignee: Matsushita Electric Industrial Company, Limited, Japan

[21] Appl. No.: 434,533

[22] Filed: Oct. 14, 1982

[30] Foreign Application Priority Data

Oct. 15, 1981 [JP] Japan .................. 56-165198
Oct. 15, 1981 [JP] Japan .................. 56-165202

[51] Int. Cl.³ .................. G01D 15/18; B05B 3/14; B05B 1/08
[52] U.S. Cl. .................. 239/102; 239/4; 346/140 R; 431/1
[58] Field of Search .................. 239/102, 4, 101, 542; 431/534, 1; 346/75, 140 PP; 261/DIG. 48; 310/DIG. 1, 328

[56] References Cited

U.S. PATENT DOCUMENTS 2,855,244  6/1955  Camp .................. 239/102
3,683,212  8/1972  Zoltan .................. 310/8.3
3,701,476 10/1972  Houser .................. 239/102
3,738,574  6/1973  Guntersdorter et al. .......... 239/102
3,747,120  7/1973  Stemme .................. 346/75
3,790,079  2/1974  Berglund et al. .................. 239/102
4,364,070 12/1982  Matsuda et al. .............. 346/140 PP Primary Examiner—Jeffrey V. Nase
Assistant Examiner—Kevin P. Weldon
Attorney, Agent, or Firm—Lowe, King, Price & Becker

[57]  ABSTRACT

An arrangement for discharging liquid droplets comprises a housing including a chamber for holding liquid therein having an intake port connected to a liquid supply container, a vibrating member secured to the housing in pressure transmitting relation with the liquid in the chamber. The vibrating member is formed with at least one nozzle opening therein through which the liquid is discharged forwardly of the housing. A piezoelectric transducer is secured to the vibrating member for inducing a rearward displacement therein to discharge a small quantity of liquid through the nozzle opening.

11 Claims, 11 Drawing Figures

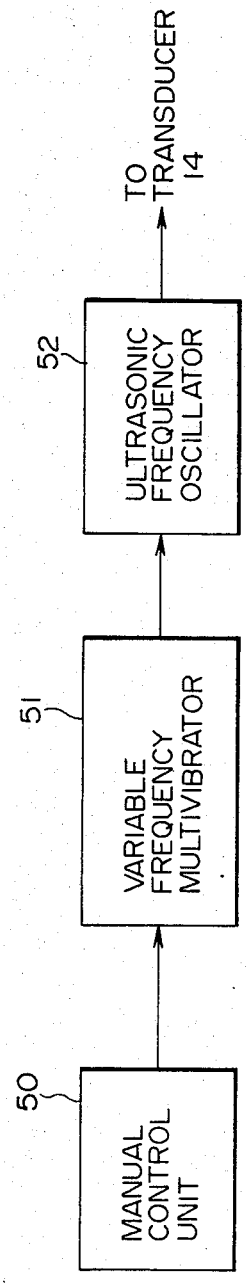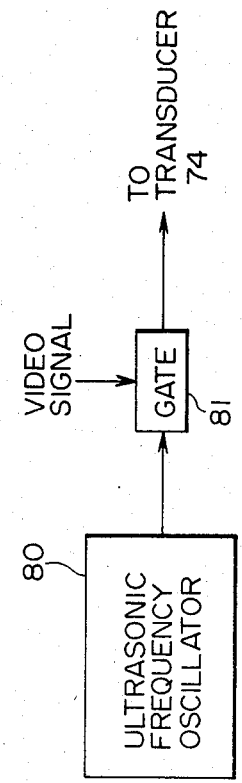

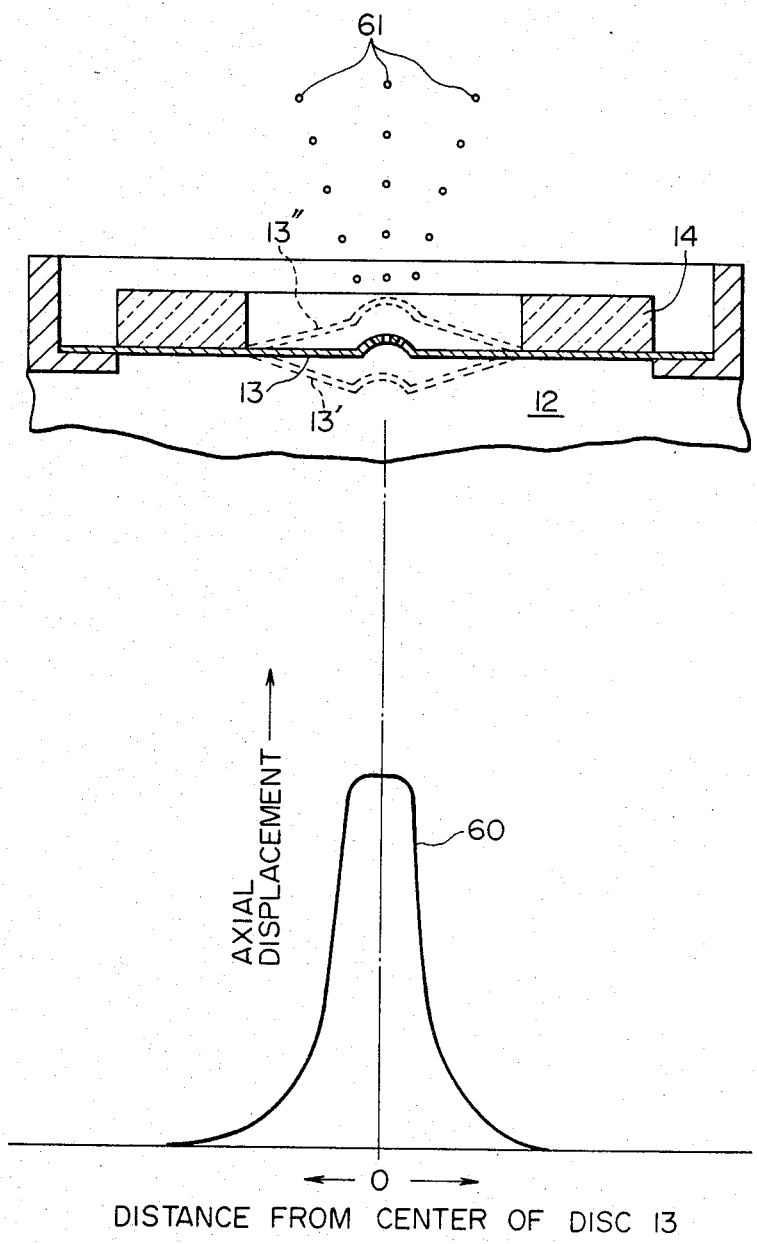

PIEZOELECTRIC OSCILLATED NOZZLE

BACKGROUND OF THE INVENTION

The present invention relates to an arrangement for discharging liquid droplets in the form of diverging streams or a single jet stream depending on various applications in which the arrangement is used. The invention is useful for universal applications including fuel burners and printers.

A piezoelectric oscillating system for effecting atomization of liquids is described in U.S. Pat. No. 3,738,574. Such a piezoelectric oscillating system comprises a piezoelectric transducer mechanically coupled by a frustum to a vibrator plate for inducing bending vibrations therein, a fluid tank and a pump for delivering fluid to the vibrating plate which is disposed at an oblique angle with respect to the force of gravity above the tank. A wick is provided to aid in diverting excess liquid from the plate to the tank. The frustum serves as a means for amplifying the energy generated by the transducer. To ensure oscillation stability, however, the frustrum needs to be machined to a high degree of precision and maintained in a correct position with respect to a conduit through which the pumped fluid is dropped on the vibrator plate and the amount of fluid to be delivered from the pump must be accurately controlled. Further disadvantages are that the system is bulky and expensive and requires high power for atomizing a given amount of fluid. In some instances 10 watts of power is required for atomizing liquid of 20 cubic centimeters per minute, and yet the droplet size is not uniform.

U.S. Pat. No. 3,683,212 discloses a pulsed liquid ejection system comprising a conduit which is connected at one end to a liquid containing reservoir and terminates at the other end in a small orifice. A tubular transducer surrounds the conduit for generating stress therein to expel a small quantity of liquid through the orifice at high speeds in the form of a stream to a writing surface.

U.S. Pat. No. 3,747,120 discloses a liquid ejection apparatus having an inner and an outer liquid chamber separated by a dividing plate having a connecting channel therein. A piezoelectric transducer is provided rearward of the apparatus to couple to the liquid in the inner chamber to generate rapid pressure rises therein to expel a small quantity of liquid in the outer chamber through a nozzle with is coaxial to the connecting channel.

While the liquid ejection systems disclosed in U.S. Pat. Nos. 3,683,212 and 3,747,120 are excellent for printing purposes due to their compact design, small droplet size and stability in the direction of discharged droplets, these systems have an inherent structural drawback in that for the liquid to be expelled through the nozzle the pressure rise generated at the rear of liquid chamber must be transmitted all the way through the bulk of liquid to the front of the chamber, so that bubbles are produced by cavitation if the liquid contains a large quantity of dissolved air. As a result satisfactory operation is not sustainted for long periods.

SUMMARY OF THE INVENTION

It is therefore an object of the invention to eliminate the problem associated with cavitation in a liquid chamber even if it contains a large quantity of dissolved air while at the same time providing a structure which is compact and inexpensive in manufacture and requires a smaller amount of power consumption.

This object is obtained by causing oscillation to occur in a vibrating member having a nozzle opening provided at the front of a liquid chamber to expel a small amount of liquid through the nozzle opening.

The present invention provides an arrangement for discharging liquid droplets which comprises a housing including a chamber for holding liquid therein having an intake port connected to a liquid supply container, a vibrating member secured to the housing in pressure transmitting relation with the liquid in the chamber and having at least one nozzle opening therein, and a piezoelectric transducer secured to the vibrating member for inducing therein a displacement to the liquid to discharge a small quantity of liquid through the nozzle opening.

According to one feature of the invention, the piezoelectric transducer is electrically polarized in the direction of thickness and formed with an aperture with which the nozzle opening is coaxially located.

According to another feature of the invention, the quantity of discharged liquid droplets and the timing of liquid ejection are easily controlled by application of a burst energy at a frequency in the range of 30 kHz to 100 kHz to the transducer, the duration of the burst being a function of a control variable which may represent the level of fuel combustion or represent the image density of a picture.

BRIEF DESCRIPTION OF THE DRAWINGS

The present invention will be described in further detail with reference to the accompanying drawings, in which:

FIG. 4 is a schematic block diagram of an electrical circuit used for stimulating the transducer of FIG. 1;

FIG. 5 is a view useful for describing the operation of the invention;

FIG. 10 is a schematic diagram of an electrical circuit for stimultating the transducer of FIG. 8.

DETAILED DESCRIPTION

Figure 1:
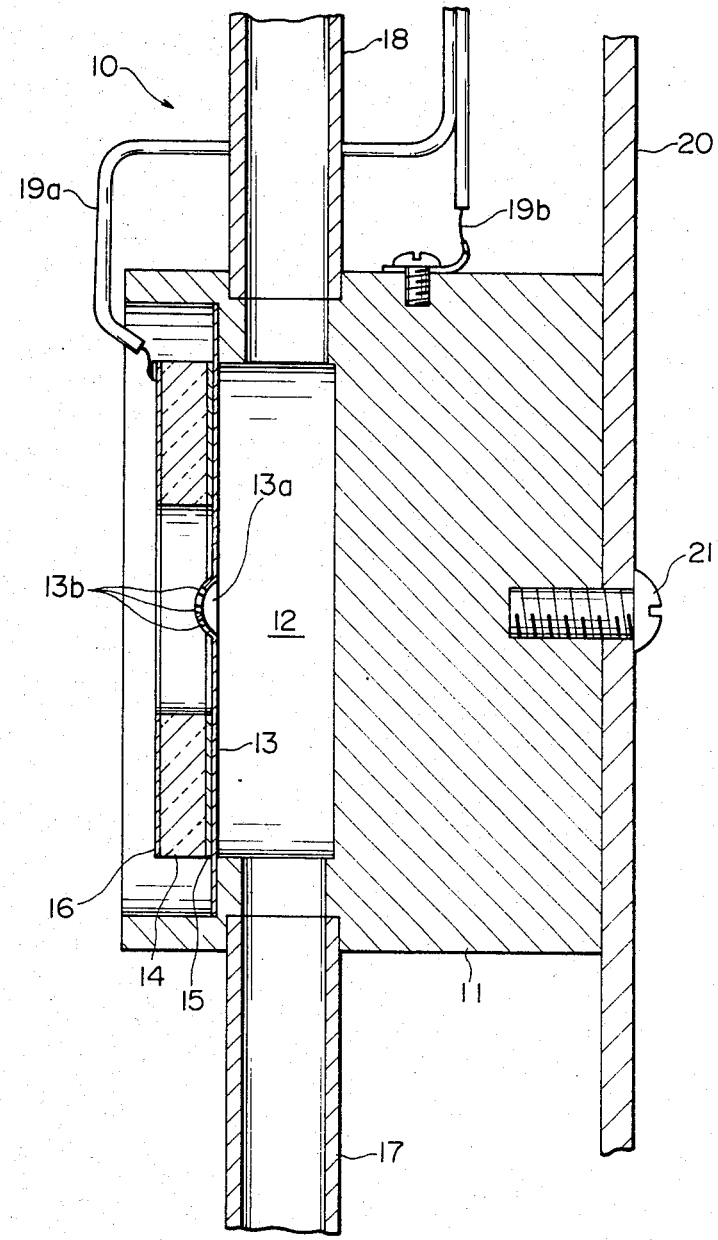
FIG. 1 is a cross-sectional view of a first preferred embodiment of the liquid ejection unit of the invention taken along the axial direction thereof.
Figure 2:
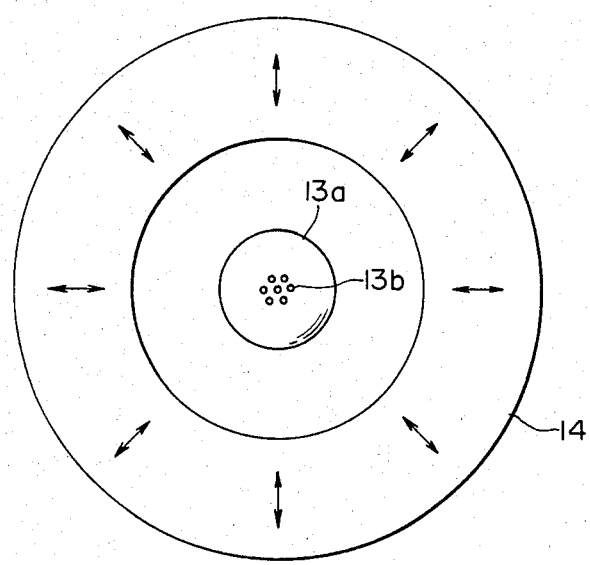
FIG. 2 is a front view of the FIG. 1 embodiment.

Referring now to FIG. 1, there is shown a first embodiment of the liquid ejection unit of the invention. The fluid ejection unit, generally indicated at 10, is particularly suitable for use in atomizing fuel or the like and comprises a metallic body 11 formed with a liquid chamber 12 having a diameter of 5 to 15 milimeters and a depth of 1 to 5 millimeters. An axially vibrating nozzle disc 13, preferably formed of a thin metal film having a thickness of 30 to 100 micrometers, is secured to the perimeter of chamber 12 front wall of body 11. To the front surface of the nozzle disc 13 is cemented a ring-shaped piezoelectric transducer 14, leaving the center portion of the nozzle disc 13 to be exposed to the outside. The transducer 14 is of a piezoelectric ceramic which is polarized in the direction of thickness so that upon application of a potential to the electrodes 15 and 16 vibration occurs therein in radial directions as illustrated in FIG. 2. The transducer 14 has an outer diameter of 5 to 15 milimeters, an inner diameter of 2 to 8 milimeters and a thickness of 0.5 to 2 milimeters. For ejecting fluids in diverging trajectories the center portion of the nozzle plate 13 is curved outward as shown at 13a and provided with a plurality of nozzle openings 13b each having a diameter of 30 to 100 micrometers. The transducer 14 is provided with a pair of film electrodes 15 and 16 on opposite surfaces thereof. The chamber 12 is in communication with a liquid supply conduit 17 which is in turn connected to a liquid supply source and is connected by a conduit 18 to an air chamber the function of which will be described later. Connections from a circuit (which will be described later) to the electrodes of the piezoelectric transducer 14 are made by wires 19a and 19b. The body 11 is secured to a wall 20 by a screw 21.

Figure 3:
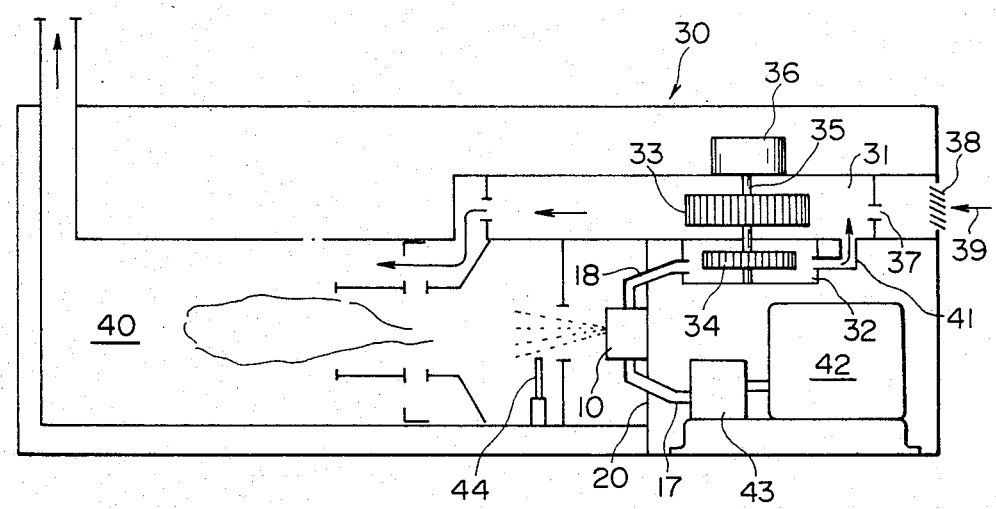
FIG. 3 is a cross-sectional view of a fuel burner in which the liquid ejection unit of FIG. 1 is mounted.

According to one application of the invention, the liquid ejection unit 10 is mounted in a fuel burner 30 as illustrated in FIG. 3. The burner 30 comprises a first chamber 31 and a second chamber 32. Fans 33 and 34 respectively located in the chambers 31 and 32 are coupled by a shaft 35 to a fan motor 36. The first chamber 31 is open at the right end to the outside through an orifice 37 and an air inlet opening 38 to draw in air as indicated by arrow 39 so that the pressure in chamber 31 is reduced below the atmospheric pressure and the downstream end of the chamber 31 is in communication with a combustion chamber 40. The second chamber 32 is connected at one end by a conduit 41 to the first chamber 31 and connected at the other end by the conduit 18 to the liquid ejection unit 10. A fuel tank 42 supplies fuel to a leveler 43 which serves to maintain the fuel supplied to the unit 10 under a constant pressure regardless of the volume of fuel in the tank 42.

When the motor 36 is not energized, the fuel in the conduit 17 stands at a level slightly below the unit 10. With the motor 36 being energized, the fan 33 causes the upstream end of first chamber 31 to drop to a subatmospheric pressure of typically −10 mmAg and the fan 34 forces air into the upstream end of first chamber 31 through conduit 41 while at the same time causing a pressure difference of typically −30 mmAg to occur between the right and left ends of second chamber 32. Therefore, the static pressure in conduit 18 drops to −40 mmAg drawing the liquid in conduit 17 upward through the chamber 12 of unit 10 into the conduit 18 and the head of the liquid therein is maintained thereafter. The chamber 12 is thus filled with liquid which is maintained at a static pressure equal to or lower than the static pressure in front of nozzle disc 13. In a typical embodiment the static pressure of the liquid is kept at −10 to −20 mmAg lower than the pressure in front of the nozzle disc. Located forwardly of the unit 10 is an ignitor 44 to cause ignition of fuel droplets. Complete combustion occurs in the combustion chamber 40 by mixture with air introduced through the first chamber 31.

FIG. 4 is an illustration of a block diagram of a circuit with which the liquid ejection unit 10 is energized for ejection of liquid droplets. The circuit comprises a manual control unit 50 which provides a fuel control signal to a variable frequency multivibrator 51 to cause it to generate a train of pulses at a frequency variable in a range between 30 to 1000 Hz as a function of the applied signal. A high frequency oscillator 52 is responsive to the output of multivibrator 51 for generating unipolar or bipolar pulses or sinusoidal waves of a constant frequency typically in a range between 30 kHz to 100 kHz for application to the transducer 14 of unit 10 in the form of bursts with a variable duty ratio proportional to the control signal from unit 50.

The operation of the liquid ejection unit 10 will be described in more detail with reference to FIG. 5.

Upon application of the high frequency burst signal to the transducer 14 vibration occurs in radial directions therein to cause nozzle disc 13 to deflect rearward as shown at 13+ to generate a pressure rise in the liquid causing it to expel forward and deflect forward as shown at 13″ to produce a pressure decrease causing the chamber 12 to suck in liquid through conduit 17. Most of the energy applied to the transducer 14 is thus converted to an axial displacement of the nozzle disc 13 having a sharp increase at the center portion of disc 13 as indicated by a curve 60 compared with the displacement at the edge thereof. Therefore, when disc 13 is deflected rearward a rapid pressure rise occurs exclusively in the portion of liquid near the nozzle openings 13b, and liquid is ejected forward in the form of diverging streams of droplets at high speeds as indicated at 61, causing a pressure decrease in liquid behind the nozzle disc 13 until the liquid pressure balances against the surface tension at the nozzle openings 13b. Due to the fact that the vibrating structure of the invention is mounted forwardly of the liquid chamber in pressure transmitting relation with the liquid, the ejection unit can be operated at such a high frequency in the range of 30 kHz to 100 kHz described above. If the liquid contains a large quantity of dissolved air cavitation would occur when the nozzle disc 13 is displaced forward. Since the vibration occurs at the forward end of the liquid chamber 12, the pressure rise tends to concentrate in the vicinity of nozzle openings 13b and bubbles tend to move away from the pressure concentrated area, so that the liquid ejecting device of the invention is unaffected by bubbles even if air is dissolved in the liquid chamber 12.

The conduit 18 also serves as a means for venting such bubbles to the outside. This arrangement is particularly useful when liquid such as kerosene is used since it contains a large amount of dissolved air.

It is found that if the static liquid pressure in chamber 12 is higher than the near atmospheric pressure immediately forward of nozzle disc 13, nozzle disc 13e fails to vibrate satisfactorily and liquid spills off. However, such undesirable circumstances are avoided by action of air chambers 31 and 32 which maintains the liquid in chamber 12 at a constant static pressure equal to or lower than the static pressure in front of the nozzle as described in connection with FIG. 3.

In a practical embodiment of the liquid ejection unit 10 for use in fuel combustion applications, sixty-one nozzle openings 13b of 80-micrometer diameter are provided in the nozzle disc 13 and the piezoelectric transducer 14 measures 10 milimeters in outer diameter and 1 milimeter in thickness. A suitable fuel for combustion applications is kerosene. The liquid ejection unit 10 operates reliably when kerosene is discharged at a rate of about 30 cubic centimeters per minute with the transducer 14 operating at a power consumption of only about 300 miliwatts.

Figure 6:
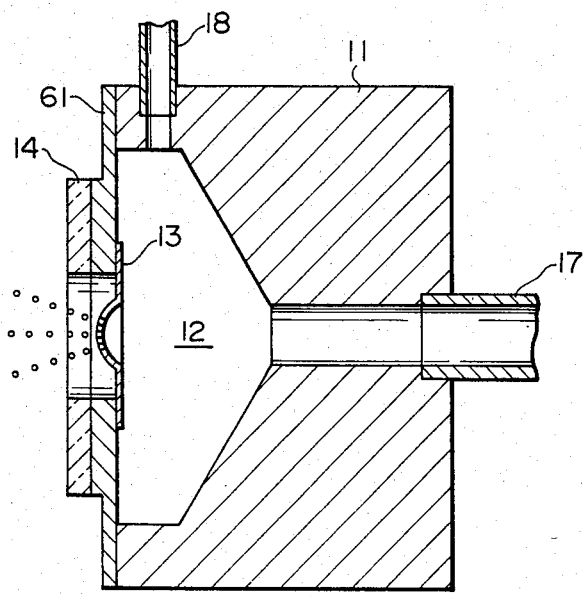
FIGS. 6 and 7 are illustrations of modifications of the embodiment of FIG. 1.
Figure 7:
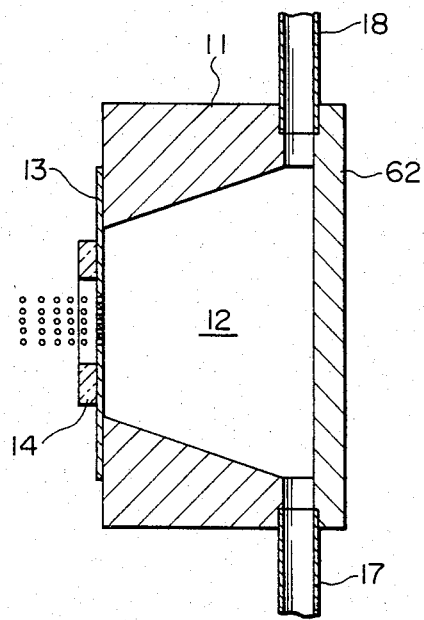

The ejection unit 10 may be modified in various ways. Such modifications are shown in FIGS. 6 and 7 in which parts corresponding to those in FIG. 1 are marked with corresponding numbers in FIG. 1. In FIG. 6, the liquid chamber 12 is generally cone-shaped with the apex of the cone being connected to the supply conduit 17 so that the latter is coaxial with the nozzle disc 13. An oscillating disc 61 is secured to the body 11 and the transducer 14 is in turn cemented to the outer surface of disc 61. The nozzle disc 13 is of a thin structure compared with the oscillating disc 61 and attached to the inside of disc 61 as illustrated. In FIG. 7 the chamber 12 is generally in the shape of a frustum of a cone with the base of the cone being closed by a rear panel 62 so that chamber 12 tapers toward nozzle disc 13. Nozzle disc 13 is of a flat member and secured to the body 11 for ejecting parallel streams of liquid droplets. Liquid supply conduit 17 and air vent conduit 18 are located adjacent to the rear panel 62. This arrangement serves to minimize the amount of loss involved in discharging liquid.

Figure 8:
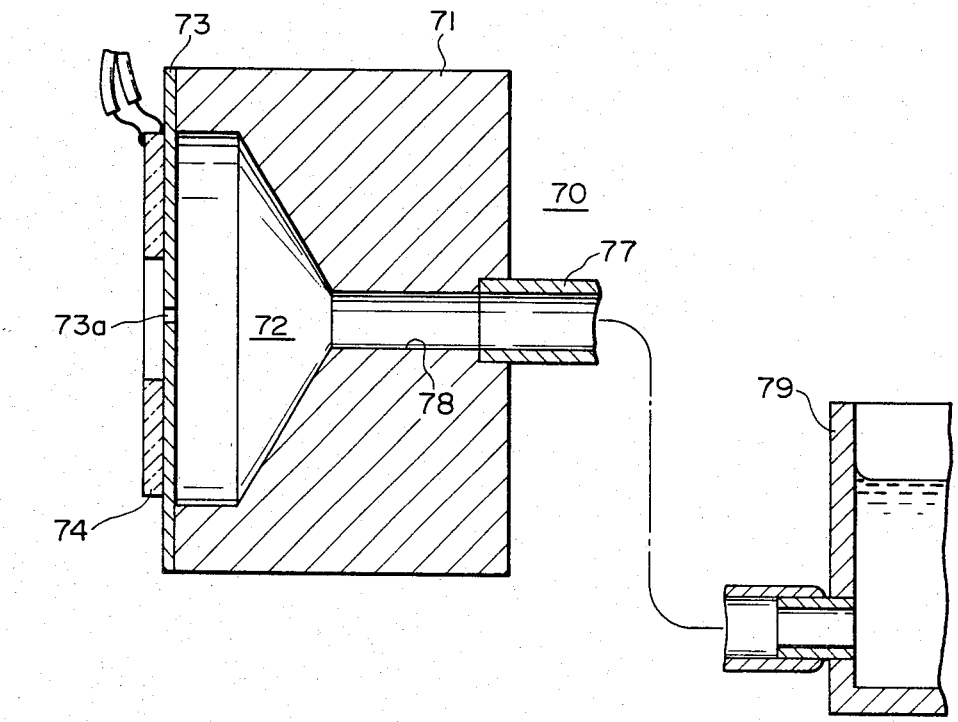
FIG. 8 is an illustration of a second preferred embodiment of the invention.
Figure 9:
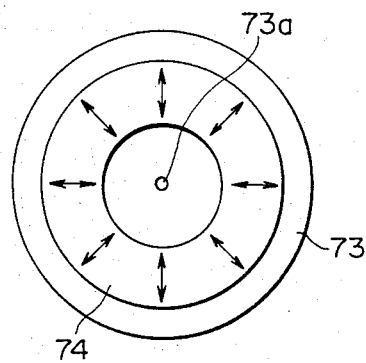
FIG. 9 is a front view of the second embodiment.

A second preferred embodiment of the liquid ejection unit, illustrated in FIGS. 8 and 9, is designed for use in ink jet printers. An ink jet ejection unit 70 comprises a body 71 having a chamber 72 of generally conical shape with the apex being connected through a channel 78 to an ink supply conduit 77. An oscillating nozzle disc 73, preferably formed of silicon, is cemented to the front edge of the body 71. A nozzle opening 73a having a diameter of 30 to 100 micrometers is formed in nozzle disc 73 in coaxial relation with the channel 78. An annular piezoelectric transducer 74 is cemented to the nozzle disc 73 as shown. The supply conduit 77 is connected to an ink container 79. This container is located in such a position relative to the ejection unit 70 that the liquid in chamber 72 is statically maintained at a pressure equal to or lower than atmospheric pressure. The liquid is constantly sucked into the chamber 72 by a pressure decrease when the vibrating member 73 is displaced forward. The transducer 14 is stimulated by an electrical signal which may be generated by a circuit shown in FIG. 10. The circuit comprises a high frequency oscillator 80 generating a carrier at a frequency in the range of 30 kHz to 100 kHz, the carrier being passed to a gate 81 to which a video signal is applied to provide a burst signal to the transducer 74.

Figure 11:
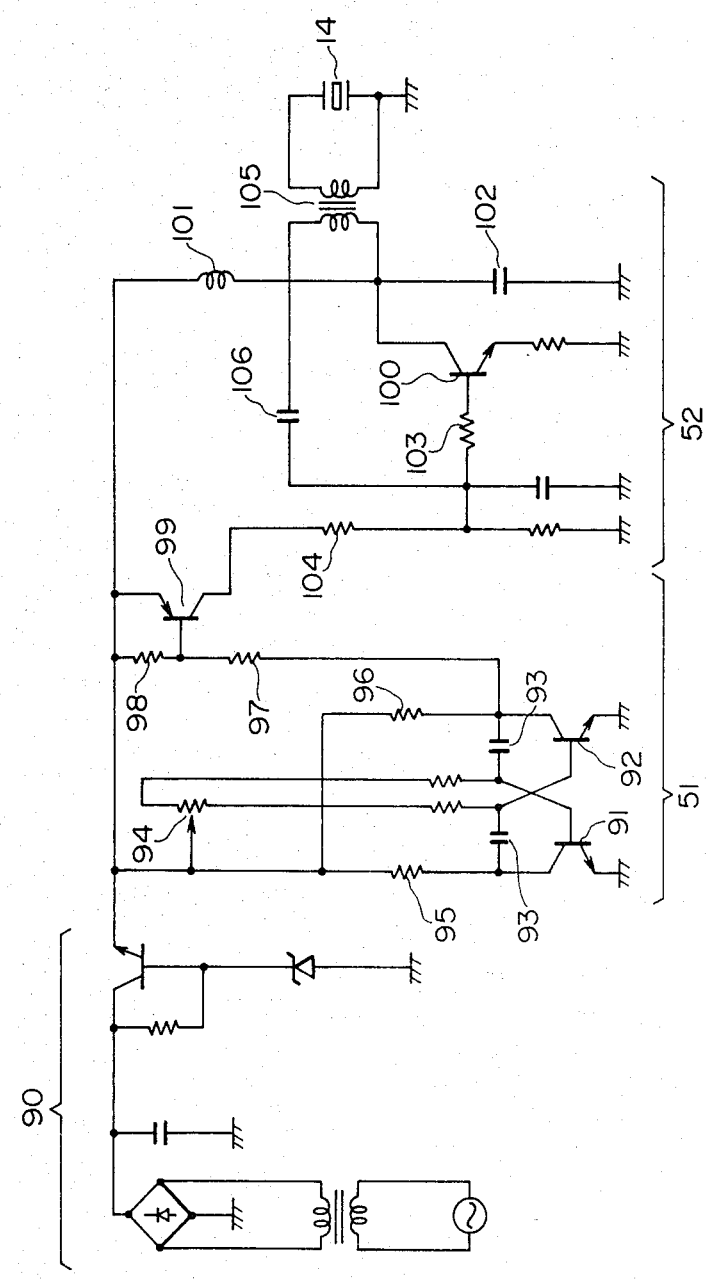
FIG. 11 is an illustration of the detail of the block diagram of FIG. 4.

FIG. 11 illustrates a practical embodiment of the circuit of FIG. 4. The variable frequency multivibrator 51 comprises a pair of emitter-grounded transistors 91 and 92 which are cross-coupled so that the base of each transistor is connected to the collector of the other through a capacitor 93. The manual control unit 50 is formed by a potentiometer 94 through which the base of transistor 91 is connected to the base of transistor 92. The wiper terminal of potentiometer 94 is connected to a voltage stabilized DC power source 90. The collectors of transistors 91, 92 are connected together by resistors 95 and 96 to the DC power source 90. The duty ratio of the multivibrator is determined by the setting of the potentiometer 94. The voltage developed at the collector of transistor 92 is coupled by voltage dividing resistors 97 and 98 to a switching transistor 99. The high frequency oscillator 52 is made up of a transistor 100 whose collector is connected to a junction between an inductor 101 and a capacitor 102 and whose base is connected through resistors 103, 104 and through the collector-emitter path of transistor 99 to the DC power source so that transistor 100 is switched on and off in accordance with the on-off time of transistor 99. The collector of transistor 100 is connected by a feedback circuit including the primary winding of a transformer 105, capacitor 106 and resistor 103 to the base thereof. The secondary winding of transformer 105 is connected to the piezoelectric transducer 14 of unit 10. An ultrasonic frequency signal (30 kHz to 100 kHz) is generated in the oscillator 52 during periods when the transistor 99 is turned on.

The foregoing description shows only preferred embodiments of the present invention. Various modifications are apparent to those skilled in the art without departing from the scope of the present invention which is only limited by the appended claims. Therefore, the embodiments shown and described are only illustrative, not restrictive.

What is claimed is:

1. An arrangement for discharging liquid droplets comprising:

a housing including a forwardly opening chamber for holding liquid therein having an intake port connected to a liquid supply container;

a vibrating member secured to a forward end of said housing defining a front wall of said chamber in rearwardly pressure transmitting relationship with the liquid in said chamber and having at least one nozzle opening therein;

means for maintaining the static pressure of said liquid in said chamber equal to or lower than the static pressure forwardly of said nozzle opening; and a piezoelectric transducer secured to said vibrating member for inducing therein a rearward displacement to cause a small quantity of liquid to be discharged forwardly through said nozzle opening.

2. An arrangement as claimed in claim 1, wherein said vibrating member has a portion curved forwardly of said housing and wherein the curved portion is formed with a plurality of nozzle openings.

3. An arrangement as claimed in claim 1, wherein said chamber is generally in the shape of a cone with the apex of the cone being connected to said liquid supply container and said vibrating member is located on the base of the cone.

4. An arrangement as claimed in claim 1, further comprising means for generating a burst signal having a duration which is a function of a control signal applied thereto, and wherein said transducer is stimulated by said burst signal.

5. An arrangement as claimed in claim 1, wherein said piezoelectric transducer is formed with an aperture and electrically polarized in the direction of thickness, and wherein said nozzle opening is located coaxially with the aperture of said transducer.

6. An arrangement as claimed in claim 5, wherein said transducer has a shape of a ring.

7. An arrangement as claimed in claim 1, wherein said pressure maintaining means maintains said housing and said liquid supply container in vertical positions relative to each other so that the static pressure in the liquid in said chamber is equal to or lower than the static pressure in front of said nozzle opening.

8. An arrangement as claimed in claim 7 wherein said pressure maintaining means maintains said liquid supply container at a position below said housing.

9. An arrangement as claimed in claim 1, wherein said pressure maintaining means includes a second port formed in said housing and means for generating a negative pressure with respect to the static pressure forwardly of said opening, said negative pressure generating means being connected through said second port to said chamber.

10. An arrangement as claimed in claim 9, wherein said chamber is generally in the shape of a frustum of a cone with the base of the cone located rearwardly of the housing and the apex of the cone being defined by said vibrating member, and wherein said intake port and said second port are located adjacent to the rear of said housing.

11. An arrangement as claimed in claim 9, wherein said pressure maintaining means comprises a vacuum chamber and means for creating a vacuum in said vacuum chamber.

* * * * *